United States Patent
Takeuchi et al.

(10) Patent No.: US 12,076,494 B2
(45) Date of Patent: Sep. 3, 2024

(54) SLEEP CONTROL APPARATUS

(71) Applicant: DAIKIN INDUSTRIES, LTD., Osaka (JP)

(72) Inventors: Toshifumi Takeuchi, Osaka (JP); Tomoyoshi Ashikaga, Osaka (JP); Chiharu Okema, Osaka (JP); Shouhei Yamada, Osaka (JP); Tomoyuki Haikawa, Osaka (JP); Yousuke Imai, Osaka (JP); Michiko Kaihotsu, Osaka (JP); Mizuho Ueno, Osaka (JP); Chizuru Murakami, Osaka (JP)

(73) Assignee: Daikin Industries, Ltd., Osaka (JP)

( * ) Notice: Subject to any disclaimer, the term of this patent is extended or adjusted under 35 U.S.C. 154(b) by 254 days.

(21) Appl. No.: 17/565,644

(22) Filed: Dec. 30, 2021

(65) Prior Publication Data

US 2022/0118216 A1  Apr. 21, 2022

Related U.S. Application Data

(63) Continuation of application No. PCT/JP2020/025618, filed on Jun. 30, 2020.

(30) Foreign Application Priority Data

Jul. 4, 2019  (JP) ................. 2019-125292

(51) Int. Cl.
*A61M 21/00* (2006.01)

(52) U.S. Cl.
CPC ..... *A61M 21/00* (2013.01); *A61M 2021/0016* (2013.01); *A61M 2021/0022* (2013.01);
(Continued)

(58) Field of Classification Search
CPC .......... A61M 21/00; A61M 2021/0016; A61M 2021/0022; A61M 2021/0027;
(Continued)

(56) References Cited

U.S. PATENT DOCUMENTS 9,978,358 B2   5/2018  Morishima
2015/0348390 A1  12/2015  Berezhnyy et al.
(Continued)

FOREIGN PATENT DOCUMENTS

JP   2007-167185 A   7/2007
JP   2014-23571 A    2/2014
(Continued)

OTHER PUBLICATIONS

Extended European Search Report for European Application No. 20834777.3, dated Jun. 19, 2023.
(Continued)

*Primary Examiner* — Brian Wilson
(74) *Attorney, Agent, or Firm* — Birch, Stewart, Kolasch & Birch, LLP

(57) ABSTRACT

A determination section of a sleep control apparatus determines an awakening point based on target data. The target data is time-series data of biological information of a target person in a target period. The target period is a period between wakefulness to failing asleep of the target person, or a period from the wakefulness of the target person to a time point at which a predetermined time has passed since the target person fell asleep. The controller controls a target device so that the target device stimulates the target person to wake up at the awakening point.

8 Claims, 3 Drawing Sheets

(52) U.S. Cl.
CPC ............. *A61M 2021/0027* (2013.01); *A61M 2021/0044* (2013.01); *A61M 2021/0066* (2013.01); *A61M 2021/0083* (2013.01)

(58) Field of Classification Search
CPC .. A61M 2021/0044; A61M 2021/0066; A61M 2021/0083; A61M 16/161; A61M 2205/3306; A61M 2205/3368; A61M 2205/505; A61M 2230/63; A61M 21/02; A61B 5/4812; G16H 40/63
See application file for complete search history.

(56) References Cited

U.S. PATENT DOCUMENTS

| | | | | |
|---|---|---|---|---|
| 2016/0151603 | A1* | 6/2016 | Shouldice | G16H 20/30 600/26 |
| 2016/0302718 | A1* | 10/2016 | Laura Lapoint | A61B 5/375 |
| 2018/0060732 | A1* | 3/2018 | Yuan | G06N 3/045 |
| 2018/0078735 | A1* | 3/2018 | Dalgleish | G06F 3/165 |

FOREIGN PATENT DOCUMENTS

| | | |
|---|---|---|
| JP | 2014-226518 A | 12/2014 |
| JP | 2016-505311 A | 2/2016 |
| JP | 2016-131574 A | 7/2016 |
| WO | WO 2017/163941 A1 | 9/2017 |

OTHER PUBLICATIONS

English translation of International Preliminary Report on Patentability and Written Opinion of the International Searching Authority for International Application No. PCT/JP2020/025618, dated Jan. 13, 2022.
International Search Report (PCT/ISA/210) issued in PCT/JP2020/025618 mailed on Aug. 11, 2020.
Written Opinion (PCT/ISA/237) issued in PCT/JP2020/025618 mailed on Aug. 11, 2020.

* cited by examiner

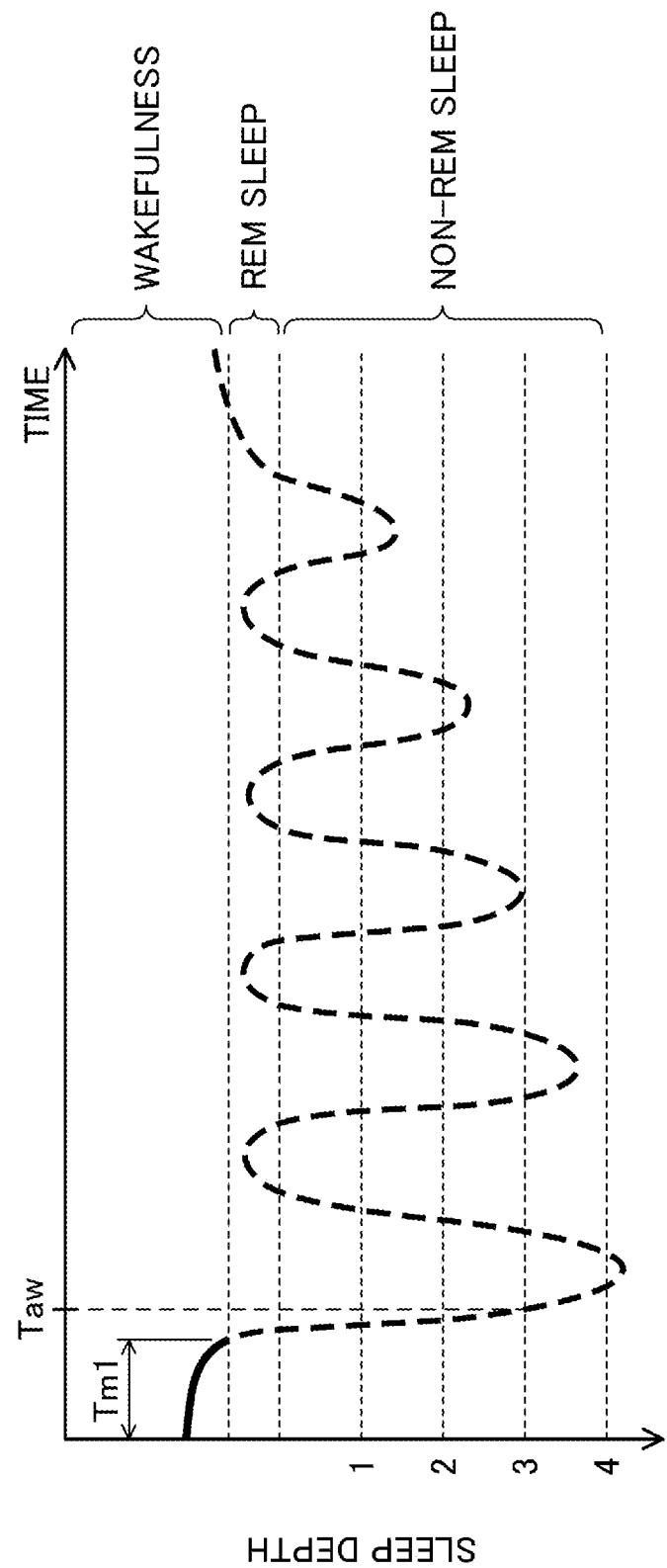

SLEEP CONTROL APPARATUS

CROSS REFERENCE TO RELATED APPLICATIONS

This application is a Continuation of PCT International Application No. PCT/JP2020/025618, filed on Jun. 30, 2020, which claims priority under 35 U.S.C § 119(a) to Japanese Patent Application No. 2019-125292, filed on Jul. 4, 2019. Each of the above applications is hereby expressly incorporated by reference, in its entirety, into the present application.

TECHNICAL FIELD

The present disclosure relates to a sleep control apparatus.

BACKGROUND ART

Patent Document 1 discloses an alarm device that informs a sleeper of awakening when a predetermined condition is met. The condition for the device to inform the sleeper of awakening includes a condition that the sleeper is in REM sleep. The device determines whether the sleeper is in REM sleep based on a determination index which is a periodic component corresponding to an ultradian rhythm of a heart rate of the sleeper.

CITATION LIST

Patent Document

PATENT DOCUMENT 1: Japanese Unexamined Patent Publication No. 2014-23571

SUMMARY

A first aspect of the present disclosure is directed to a sleep control apparatus (10). The sleep control apparatus (10) includes: a biological information acquisition section (21) configured to acquire biological information of a target person (60); a determination section (31) configured to determine an awakening point based on target data (42) which is time-series data of the biological information of the target person (60) acquired by the biological information acquisition section (21) in a predetermined target period, the awakening point being a time point after the target period has passed and at which the target person (60) is awakened; and a controller (36) configured to control a predetermined target device (57) so that the target device (57) stimulates the target person (60) to wake up at the awakening point determined by the determination section (31). The target period is a period between wakefulness to falling asleep of the target person (60), or a period from the wakefulness of the target person (60) to a time point at which a predetermined time has passed since the target person (60) fell asleep.

BRIEF DESCRIPTION OF THE DRAWINGS

FIG. 3 is a graph showing an example of prediction data generated by a prediction data generator according to the embodiment.

DESCRIPTION OF EMBODIMENTS

An embodiment will be described below. A sleep control apparatus (10) of the present embodiment is an apparatus that awakens a target person (60) sleeping, especially taking a nap, at the right timing.

Figure 1:
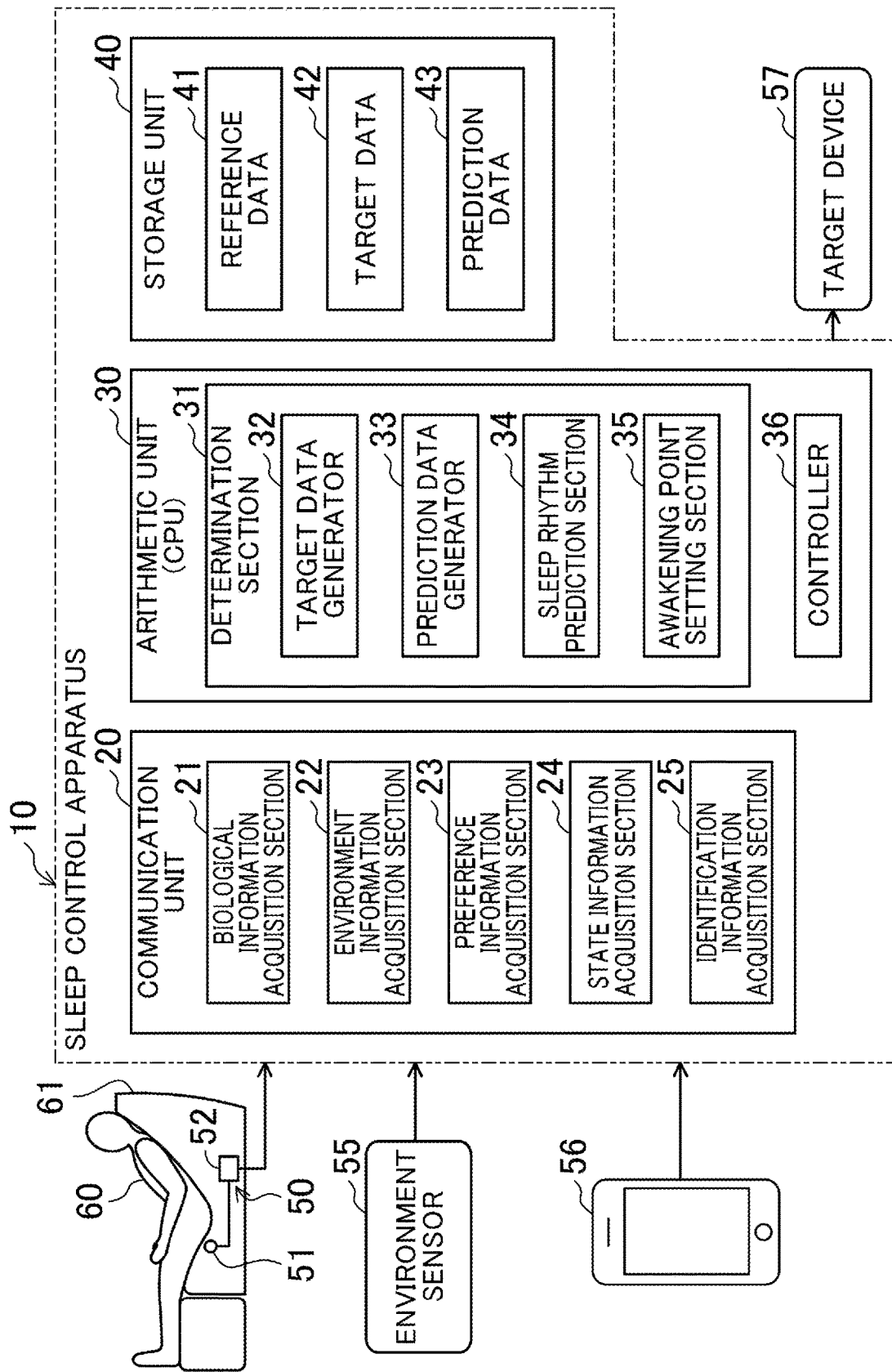
FIG. 1 is a block diagram illustrating a configuration of a sleep control apparatus according to an embodiment.

As illustrated in FIG. 1, the sleep control apparatus (10) of the present embodiment communicates via wires or wirelessly with a body motion sensor (50), an environment sensor (55), an information terminal (56), and a target device (57) to be controlled by the sleep control apparatus (10). The sleep control apparatus (10) mainly acquires information from the body motion sensor (50), the environment sensor (55), and the information terminal (56), and outputs a control signal to the target device (57).

—Body Motion Sensor—

The body motion sensor (50) includes a pressure sensitive section (51) and a signal processor (52). The body motion sensor (50) is installed in a couch (61) on which the target person (60) takes a nap. The body motion sensor (50) detects a body motion accompanying body processes of the target person (60), e.g., a heartbeat, breathing, and turning over in bed, and outputs biological information of the target person (60) obtained by processing a signal (body motion signal) related to the detected body motion.

Although not shown, the pressure sensitive section (51) includes a flexible tube made of resin and a sensor provided at one end of the tube. The tube of the pressure sensitive section (51) is arranged to cross the seat of the couch (61). An internal pressure of the tube varies depending on the body motion of the target person (60) lying on the couch (61). The sensor is a microphone that converts the change in the internal pressure of the tube into an electrical signal. The electrical signal outputted by the sensor is the body motion signal of the target person (60).

The signal processor (52) processes the body motion signal outputted from the sensor of the pressure sensitive section (51), and extracts biological information of the target person (60) from the body motion signal. The biological information of the target person (60) obtained by the signal processor (52) is time-series data of the target person (60) per unit time, such as a heart rate, a respiration rate, and a body motion frequency. The signal processor (52) transmits the obtained biological information of the target person (60) to the sleep control apparatus (10).

The body motion sensor (50) is not limited to be installed in the couch (61). The body motion sensor (50) may be provided for an object that the target person (60) uses to sleep. Examples of the object to be provided with the body motion sensor (50) include a bed on which the target person (60) lies, a sofa or an easy chair on which the target person (60) sits in a relaxed posture.

—Environment Sensor—

The environment sensor (55) includes a plurality of sensors that measure indexes related to the environment of the space where the couch (61) on which the target person (60) lies is placed. Examples of the sensors constituting the environment sensor (55) include a temperature sensor for measuring indoor air temperature, a humidity sensor for measuring indoor air humidity, an illuminance sensor for measuring indoor brightness, a wind speed sensor for measuring indoor wind speed, and a noise sensor for measuring indoor noise. Each sensor constituting the environment sensor (55) transmits a measurement value to the sleep control apparatus (10).

The sensors constituting the environment sensor (55) are selected depending on the type of the target device (57) to be controlled by the sleep control apparatus (10). For example, when the target device (57) includes an air conditioner, at least a temperature sensor that measures the indoor air temperature constitutes the environment sensor (55). When the target device (57) includes an illuminator, at least an illuminance sensor that measures the indoor brightness constitutes the environment sensor (55).

—Information Terminal—

The information terminal (56) is, for example, a smartphone or a tablet personal computer. A predetermined application program is installed in the information terminal (56). The information terminal (56) functions as a preference information input section and a state information input section by executing the application program.

The information terminal (56) functioning as the preference information input section can receive input preference information on the preference of the target person (60) in the environment. The preference information is, for example, information on the preference of the target person (60) in the indoor air temperature, the indoor air humidity, the indoor brightness, and the color of illumination.

The information terminal (56) functioning as the state information input section can receive state information on the state of the target person (60) sleeping or after awakening. The state information is, for example, information on comfortability during sleep, e.g., it was hot or cold during sleep, and the feeling of the subject after awakening, e.g., the subject feels refreshed, or wishes to sleep more.

The information terminal (56) can also receive identification information for identifying the target person (60) who has entered the preference information and the state information to the information terminal (56). The identification information is, for example, an employee number unique to the target person (60). The information terminal (56) transmits the preference information, state information, and identification information of the target person (60) inputted to the information terminal (56) to the sleep control apparatus (10).

—Target Device—

The target device (57) is a device to be controlled by the sleep control apparatus (10) of the present embodiment. The target device (57) is capable of stimulating the target person (60) to wake up.

Examples of the target device (57) include a device that stimulates the target person (60) with sound, such as a buzzer, a chime, and an audio device, a device that stimulates the target person (60) with temperature, such as an air conditioner for conditioning the indoor space, a device that stimulates the target person (60) with light, such as an illuminator placed in the room, a device that stimulates the target person (60) with scent, such as an aroma diffuser for emitting aromatic components of aromatic oil, and a device that physically stimulates the target person (60), such as a vibrator that shakes the target person, and a reclining device that raises the target person's body. The target device (57) may include one or more devices.

—Sleep Control Apparatus—

The sleep control apparatus (10) includes a communication unit (20), an arithmetic unit (30), and a storage unit (40).

<Communication Unit>

The communication unit (20) is a communication module that communicates with the body motion sensor (50), the environment sensor (55), the information terminal (56), and the target device (57). The communication unit (20) includes a biological information acquisition section (21), an environment information acquisition section (22), a preference information acquisition section (23), a state information acquisition section (24), and an identification information acquisition section (25).

The biological information acquisition section (21) receives biological information of the target person (60) outputted by the signal processor of the body motion sensor (50), and transmits the received biological information of the target person (60) to the arithmetic unit (30). The environment information acquisition section (22) receives measurement values outputted from various sensors constituting the environment sensor (55), and transmits the received measurement values to the storage unit (40) as environment information. The preference information acquisition section (23) receives the preference information outputted from the information terminal (56) and transmits the received preference information to the storage unit (40). The state information acquisition section (24) receives the state information outputted from the information terminal (56) and transmits the received state information to the storage unit (40). The identification information acquisition section (25) receives the identification information outputted by the information terminal (56) and transmits the received identification information to the storage unit (40).

<Storage Unit>

The storage unit (40) is, for example, a semiconductor memory including an integrated circuit. The storage unit (40) stores a program for allowing the arithmetic unit (30) to execute a predetermined operation, and data necessary for the operation of the arithmetic unit (30).

The storage unit (40) stores reference data (41) acquired in advance, and target data (42) and prediction data (43) generated by the arithmetic unit (30). The storage unit (40) stores the environment information, the preference information, the state information, and the identification information transmitted from the communication unit (20). The storage unit (40) stores the preference information and the state information in association with the identification information of the target person (60) who has entered the preference information and the state information to the information terminal (56).

<Arithmetic Unit>

The arithmetic unit (30) is, for example, a microprocessor including an integrated circuit. The arithmetic unit (30) functions as a determination section (31) and a controller (36) when executing a program stored in the storage unit (40).

The determination section (31) includes a target data generator (32), a prediction data generator (33), a sleep rhythm prediction section (34), and an awakening point setting section (35). The determination section (31) determines an awakening point Taw at which the target person (60) is awakened based on the reference data (41) and the target data (42) stored in the storage unit (40). Each of the target data generator (32), prediction data generator (33), sleep rhythm prediction section (34), and awakening point setting section (35) of the determination section (31) performs a predetermined operation to determine the awakening point Taw.

The controller (36) generates a control signal for controlling the target device (57). The control signal generated by the controller (36) is a signal that instructs the target device (57) to perform an operation of giving the target person (60) a stimulus that awakens the target person (60) at the awakening point Taw. The communication unit (20) transmits the control signal generated by the controller (36) to the target device (57).

—Operation of Sleep Control Apparatus—

How the sleep control apparatus (10) operates will be described below. Operations performed by the arithmetic unit (30) will be mainly described below. The reference data (41) stored in the storage unit (40) will also be described.

<Target Data Generator of Determination Section>

The target data generator (32) of the determination section (31) generates the target data (42) using the biological information of the target person (60) that the biological information acquisition section (21) has received from the body motion sensor (50). The target data (42) is time-series data of the biological information of the target person (60) outputted by the body motion sensor (50) in a predetermined target period Tm1.

The target period Tm1 for the target data generator (32) of the present embodiment is a period from when the target person (60) lies on the couch (61) to when the target person (60) falls asleep. The target data generator (32) generates data of the biological information received from the body motion sensor (50) for the target period Tm1, i.e., the biological information of the target person (60) lying on the couch (61) for the target period Tm1, in association with time when the biological information was detected, and stores the data as the target data (42) in the storage unit (40).

<Prediction Data Generator of Determination Section>

Figure 2:
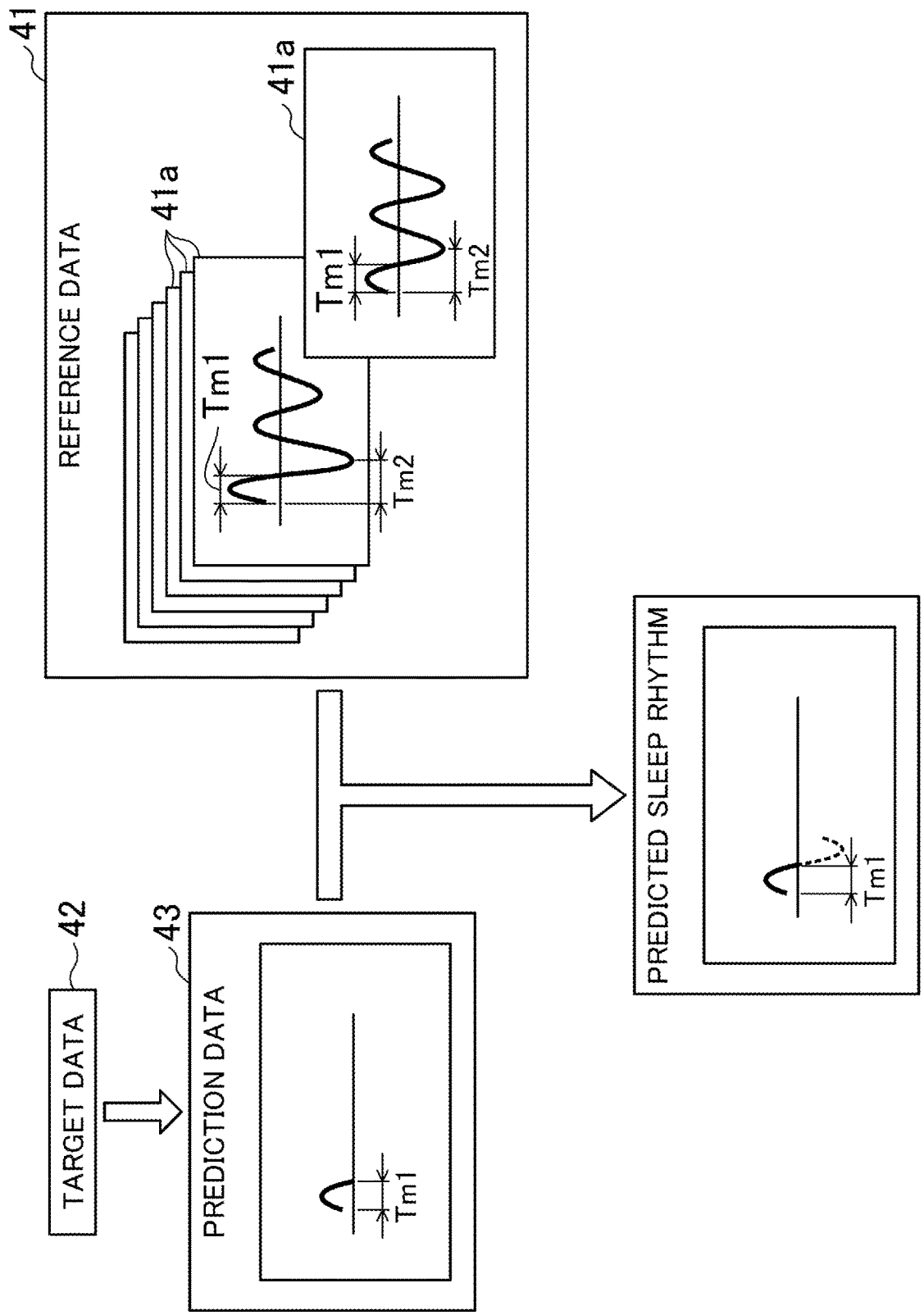
FIG. 2 is a diagram illustrating how a determination section of an arithmetic unit according to the embodiment operates.

As illustrated in FIG. 2, the prediction data generator (33) of the determination section (31) generates the prediction data (43) using the target data (42) stored in the storage unit (40). Specifically, the prediction data generator (33) reads the target data (42) from the storage unit (40), and performs arithmetic processing using the biological information included in the read target data (42) to calculate the sleep depth of the target person (60). Then, the prediction data generator (33) generates time-series data of the sleep depth of the target person (60) in the target period Tm1, and stores the time-series data in the storage unit (40) as the prediction data (43).

<Reference Data>

The reference data (41) stored in the storage unit (40) is data generated for a plurality of subjects including humans other than the target person (60). This reference data (41) is stored in advance in the storage unit (40) before the determination section (31) performs a predetermined operation for the target person (60) lying on the couch (61).

As illustrated in FIG. 2, the reference data (41) is a set of sub data (41a) acquired from different subjects. Each sub data (41a) represents a sleep rhythm of one subject, i.e., time-series data representing a temporal change in sleep depth. Each sub data (41a) of the reference data (41) is associated with the environment information on the environment of the space where the subject was sleeping at the time of acquisition of the sub data (41a), e.g., temperature, humidity, and illuminance of the space.

Each sub data (41a) is time-series data of the sleep depth in a period before and after the falling asleep of the subject. Each sub data (41a) is preferably time-series data including a first sleep cycle that comes first after the subject fell sleep. Each sub data (41a) needs to include at least time-series data in an essential period Tm2. The essential period Tm2 is a period between wakefulness of the subject and a time point at which the sleep depth shifts to a shallower stage after going through to a deeper stage.

The reference data (41) may include data generated in advance for the exact target person (60) lying on the couch (61). The reference data (41) is preferably generated for as many subjects as possible, e.g., several hundred subjects or more.

<Sleep Rhythm Prediction Section of Determination Section>

As illustrated in FIG. 2, the sleep rhythm prediction section (34) of the determination section (31) generates a predicted sleep rhythm based on the prediction data (43) and the reference data (41). The predicted sleep rhythm is time-series data of sleep depth that includes a predicted value of a temporal change in sleep depth of the target person (60) after the target period Tm1.

More specifically, the sleep rhythm prediction section (34) selects, from the set of sub data (41a) constituting the reference data (41), some sub data (41a) in which the "temporal change in sleep depth in the target period Tm1" is approximate to the prediction data (43). Then, from the selected sub data (41a), the sleep rhythm prediction section (34) selects one sub data (41a) in which the corresponding environment information is the closest to the environment information at the time of acquisition of the target data (42). Then, the sleep rhythm prediction section (34) sets the "temporal change in sleep depth after the target period Tm1" in the finally selected one sub data (41a) as the predicted value of the "temporal change in sleep depth after the target period Tm1" for the target person (60) lying on the couch (61). This predicted value is indicated by a dotted curve in the predicted sleep rhythm shown in FIG. 2.

<Awakening Point Setting Section of Determination Section>

The awakening point setting section (35) of the determination section (31) determines an awakening point Taw, which is a time point at which the target person (60) is awakened, based on the predicted sleep rhythm generated by the sleep rhythm prediction section (34). The awakening point Taw is a time point after the target period Tm1 has passed. The awakening point Taw is a time point within a period in which the sleep depth of the target person (60) gradually shifts to a deeper stage after the target person (60) fell asleep.

As illustrated in FIG. 3, the awakening point setting section (35) sets, as the awakening point Taw, a time point at which the sleep depth first reaches a predetermined value ("3" in the present embodiment) in the predicted sleep rhythm after the falling asleep of the target person (60). The awakening point Taw is specified by, for example, time elapsed from the falling asleep of the target person (60) to the awakening point Taw.

<Controller>

The controller (36) generates a control signal for controlling the operation of the target device (57). The control signal generated by the controller (36) is a signal that instructs the target device (57) to perform a predetermined operation to give the target person (60) a stimulus that awakens the target person (60) at the awakening point Taw determined by the determination section (31). The control signal generated by the controller (36) is transmitted from the communication unit (20) to the target device (57).

Specific examples of the control signal will be described below. When the target device (57) is "a device that stimulates the target person (60) with sound," the controller (36) generates a control signal that instructs the target device (57) "to make a sound at the awakening point Taw." When the target device (57) is "a device that stimulates the target person (60) with temperature," the controller (36) generates a control signal that instructs the target device (57) "to gradually lower or raise the indoor air temperature a predetermined time before the awakening point Taw." When the target device (57) is a "device that stimulates the target person (60) with light," the controller (36) generates a control signal that instructs the target device (57) "to gradually increase the indoor illuminance a predetermined time before the awakening point Taw." When the target device (57) is a "device that stimulates the target person (60) with scent," the controller (36) generates a control signal that instructs the target device (57) "to start releasing aromatic components to the indoor space a predetermined time before the awakening point Taw." When the target device (57) is "a device that physically stimulates the target person (60)," the controller (36) generates a control signal that instructs the target device (57) "to generate a physical stimulus, such as vibration, at the awakening point Taw."

The controller (36) can output control signals to two or more target devices (57). In this case, the controller (36) generates a control signal corresponding to each target device (57). Then, the controller (36) transmits the generated control signals to the target devices (57) respectively corresponding the control signals through the communication unit (20).

When determining the details of the control signal, the controller (36) refers to the preference information stored in the storage unit (40). For example, when the preference information includes information indicating that "the target person (60) easily feels cold," the controller (36) transmits the control signal to the air conditioner as the target device (57) to instruct the air conditioner to "reduce the decrease in the room temperature." When the preference information includes information indicating that "the target person (60) prefers warm color," the controller (36) transmits the control signal to the illuminator as the target device (57) to instruct the illuminator to "emit warm color light."

When determining the details of the control signal, the controller (36) also refers to the state information and the identification information stored in the storage unit (40). Specifically, the controller (36) acquires the identification information of the target person (60) lying on the couch (61), and reads the state information associated with the same identification information as the acquired identification information from the storage unit (40). For example, when the read state information includes information indicating "the target person felt hot (last time)," the controller (36) outputs a control signal including an instruction to lower the indoor air temperature faster than the last use by the target person (60) to the air conditioner as the target device (57). When the read state information includes information indicating "the target person felt refreshed (last time)," the controller (36) outputs a control signal including the same instruction as the signal outputted in the last use by the target person (60) to the target device (57).

—Feature (1) of Embodiment—

The sleep control apparatus (10) of the present embodiment includes a biological information acquisition section (21), a determination section (31), and a controller (36). The biological information acquisition section (21) acquires biological information of the target person (60). The determination section (31) determines an awakening point Taw based on target data (42) which is time-series data of the biological information of the target person (60) acquired by the biological information acquisition section (21) in a predetermined target period Tm1. The awakening point Taw is a time point after the target period Tm1 has passed and at which the target person (60) is awakened. The controller (36) controls a predetermined target device (57) so that the target device (57) stimulates the target person (60) to wake up at the awakening point Taw determined by the determination section (31). The target period Tm1 is a period between wakefulness to falling asleep of the target person (60).

The determination section (31) of the sleep control apparatus (10) of the present embodiment determines the awakening point Taw based on the target data (42). The target data (42) is time-series data of the biological information of the target person (60) in the target period Tm1 including a period of wakefulness of the target person (60). The awakening point Taw is a time point at which the target person (60) is awakened after the target period Tm1 has passed. Thus, the sleep control apparatus of the present embodiment can wake up the target person (60) at the right timing even when a period between the falling asleep of the target person (60) and the awakening point Taw is relatively short.

—Feature (2) of Embodiment—

The determination section (31) of the sleep control apparatus (10) of the present embodiment determines the awakening point Taw based on reference data (41) and the target data (42). The reference data (41) is time-series data of the biological information acquired in advance from a plurality of subjects in a period before and after the falling asleep of each subject.

The determination section (31) of the sleep control apparatus (10) of the present embodiment determines the awakening point Taw based on the reference data (41) related to the plurality of subjects including humans other than the target person (60) and the target data (42) related to the target person (60). Thus, the sleep control apparatus can awaken the target person (60) at the right timing without acquiring information on the sleep of the target person (60) in advance.

—Feature (3) of Embodiment—

The determination section (31) of the sleep control apparatus (10) of the present embodiment predicts a temporal change in sleep depth of the target person (60) after the lapse of the target period Tm1 based on the target data (42) and the reference data (41), and determines the awakening point Taw based on the predicted temporal change in the sleep depth of the target person (60).

The determination section (31) of the present embodiment predicts the "temporal change in the sleep depth of the target person (60)" used for determining the awakening point Taw based on the target data (42) and the reference data (41).

—Feature (4) of Embodiment—

The determination section (31) of the sleep control apparatus (10) of the present embodiment determines, as the awakening point Taw, a time point at which the sleep depth of the target person (60) reaches a predetermined value in the predicted temporal change in the sleep depth of the target person (60).

The determination section (31) of the present embodiment determines the awakening point Taw based on the predicted "temporal change in the sleep depth of the target person (60)."

—Feature (5) of Embodiment—

The determination section (31) of the sleep control apparatus (10) of the present embodiment determines, as the awakening point Taw, a time point within a period in which the sleep depth of the target person (60) shifts to a deeper stage after the target person (60) fell asleep.

The determination section (31) of the present embodiment determines, as the awakening point Taw, a time point at which the sleep depth of the target person (60) first reaches the deepest stage after the target person (60) fell asleep.

Thus, the sleep control apparatus of the present embodiment can wake up the target person (60) at a timing suitable for a nap.

—Feature (6) of Embodiment—

The sleep control apparatus (10) of the present embodiment includes an environment information acquisition section (22) that acquires environment information on the environment around the target person (60). The determination section (31) determines the awakening point Taw based on the environment information acquired by the environment information acquisition section (22) and the target data (42).

The determination section (31) of the sleep control apparatus (10) of the present embodiment determines the awakening point Taw based on at least the target data (42) and the environment information. Thus, the sleep control apparatus of the present embodiment can wake up the target person (60) at the right timing taking the environment around the target person (60) into consideration.

—Feature (7) of Embodiment—

The sleep control apparatus (10) of the present embodiment includes a preference information acquisition section (23) that acquires preference information on the preference of the target person (60) in the environment. The controller (36) determines the details of control of the target device (57) based on the preference information acquired by the preference information acquisition section (23).

The controller (36) of the present embodiment determines the details of control of the target device (57) based on the preference information. This configuration can stimulate the target person (60) to wake up in accordance with the preference of the target person (60).

—Feature (8) of Embodiment—

The sleep control apparatus (10) of the present embodiment includes a state information acquisition section (24) that acquires state information on the state of the target person (60) sleeping or after awakening. The controller (36) determines details of control of the target device (57) based on the state information acquired by the state information acquisition section (24).

The controller (36) of the sleep control apparatus (10) of the present embodiment determines the details of control of the target device (57) based on the state information. This can improve the state of the target person (60) sleeping or after awakening when the target person (60) next uses the sleep control apparatus (10).

—First Variation of Embodiment—

As described above, the target data (42) generated by the target data generator (32) is time-series data of the biological information of the target person (60) outputted by the body motion sensor (50) in a predetermined target period Tm1. The target period Tm1 may be a period before and after the falling asleep of the target person (60). Specifically, the target period Tm1 may be a period from "when the target person (60) lies on the couch (61)" to "when a predetermined time, e.g., several minutes, has passed since the target person (60) fell asleep."

—Second Variation of Embodiment—

The sleep rhythm prediction section (34) of the present embodiment may be configured to generate a predicted sleep rhythm by what is called machine learning.

The storage unit (40) of the sleep control apparatus (10) of this variation stores a learned model instead of the reference data (41). The sleep rhythm prediction section (34) of the present variation inputs the target data (42) to the learned model and sets the data thus obtained as the predicted sleep rhythm.

A process of creating a learned model of this variation will be described below. First, a set of sub data (41a) same as that described above is acquired from a plurality of subjects. Specifically, for each of the subjects, time-series data indicating "temporal change in the sleep depth of the subject in a period before and after the falling asleep of the subject" is acquired. This time-series data is referred to as subject data. Part of the subject data, i.e., "time-series data of the subject's sleep depth" in a period corresponding to the target period Tm1, is used as input data. The whole subject data is used as teaching data. Then, a learned model is created using the input data and the teaching data.

—Third Variation of Embodiment—

The storage unit (40) of the sleep control apparatus (10) of the present embodiment does not need to be installed at the same place as the communication unit (20) and the arithmetic unit (30). For example, the storage unit (40) may be provided in a cloud server at a location remote from the communication unit (20) and the arithmetic unit (30). In this case, the storage unit (40) communicates with the communication unit (20) and the arithmetic unit (30) via a communication line such as the Internet.

While the embodiments and variations thereof have been described above, it will be understood that various changes in form and details may be made without departing from the spirit and scope of the claims. The foregoing embodiments and variations thereof may be combined and replaced with each other without deteriorating the intended functions of the present disclosure.

INDUSTRIAL APPLICABILITY

As can be seen from the foregoing description, the present disclosure is useful for a sleep control apparatus.

EXPLANATION OF REFERENCES

10 Sleep Control Apparatus
21 Biological Information Acquisition Section
22 Environment Information Acquisition Section
23 Preference Information Acquisition Section
24 State Information Acquisition Section
31 Determination Section
36 Controller
41 Reference Data
42 Target Data
57 Target Device
60 Target Person

The invention claimed is:

1. A sleep control apparatus, comprising:
a biological information acquisition section configured to acquire biological information of a target person;
a determination section configured to determine an awakening point based on target data which is time-series data of the biological information of the target person acquired by the biological information acquisition section in a predetermined target period, the awakening point being a time point after the target period has passed and at which the target person is awakened; and
a controller configured to control a predetermined target device so that the target device stimulates the target person to wake up at the awakening point determined by the determination section, wherein
the target period is a period between wakefulness to falling asleep of the target person, or a period from the wakefulness of the target person to a time point at which a predetermined time has passed since the target person fell asleep, the determination section determines the awakening point based on reference data which is time-series data of the biological information acquired in advance from a plurality of subjects in a period before and after the falling sleep of each subject and the target data, and the reference data includes time-series data including a first sleep cycle that comes first after each subject fell asleep.

2. The sleep control apparatus of claim 1, wherein the determination section predicts a temporal change in sleep depth of the target person after the lapse of the target period based on the target data and the reference data, and determines the awakening point based on the predicted temporal change in the sleep depth of the target person.

3. The sleep control apparatus of claim 2, wherein the determination section determines, as the awakening point, a time point at which the sleep depth of the target person reaches a predetermined value in the predicted temporal change in the sleep depth of the target person.

4. The sleep control apparatus of claim 1, wherein the determination section determines, as the awakening point, a time point within a period in which sleep depth of the target person shifts to a deeper stage after the target person fell asleep.

5. The sleep control apparatus of claim 1, further comprising:
   an environment information acquisition section configured to acquire environment information on an environment around the target person, wherein
   the determination section determines the awakening point based on the environment information acquired by the environment information acquisition section and the target data.

6. The sleep control apparatus of claim 1, further comprising:
   a preference information acquisition section configured to acquire preference information on preference of the target person in an environment, wherein
   the controller determines details of control of the target device based on the preference information acquired by the preference information acquisition section.

7. The sleep control apparatus of claim 1, further comprising:
   a state information acquisition section configured to acquire state information on the state of the target person sleeping or after awakening, wherein
   the controller determines details of control of the target device based on the state information acquired by the state information acquisition section.

8. The sleep control apparatus of claim 1, wherein the determination section predicts a temporal change in sleep depth of the target person after the lapse of the target period based on the target data and the reference data, generates a predicted sleep rhythm including a predicted value of a temporal change in sleep depth of the target person after the lapse of the target period, and determines the awakening point based on a predicted value of the temporal change in sleep depth of the target person included in the predicted sleep rhythm.

* * * * *